United States Patent
Freed et al.

(10) Patent No.: US 7,280,873 B2
(45) Date of Patent: *Oct. 9, 2007

(54) TREATMENT OF OROPHARYNGEAL DISORDERS BY APPLICATION OF NEUROMUSCULAR ELECTRICAL STIMULATION

(75) Inventors: Marcy L. Freed, Marysville, WA (US); Leonard A. Freed, Kailua, HI (US); Michael O. Christian, Mayfield Heights, OH (US); Howard Tucker, Cleveland Heights, OH (US); Bernard Kotton, Beachwood, OH (US); Erol M. Beytas, Beachwood, OH (US); Marie Asmar, Richmond Heights, OH (US); Ed Dunlay, Harrison, TN (US); Tim Kretschmer, Wabasha, MN (US)

(73) Assignee: ESD, LLC, Marysville, WA (US)

( * ) Notice: Subject to any disclaimer, the term of this patent is extended or adjusted under 35 U.S.C. 154(b) by 633 days.

This patent is subject to a terminal disclaimer.

(21) Appl. No.: 10/782,620

(22) Filed: Feb. 18, 2004

(65) Prior Publication Data
US 2004/0220645 A1 Nov. 4, 2004

Related U.S. Application Data

(63) Continuation-in-part of application No. 10/375,407, filed on Feb. 27, 2003, now Pat. No. 7,039,468, which is a continuation-in-part of application No. 10/308,105, filed on Dec. 3, 2002, now abandoned, which is a continuation of application No. 09/757,804, filed on Jan. 11, 2001, now abandoned, which is a continuation of application No. 09/236,829, filed on Jan. 25, 1999, now Pat. No. 6,198,970, which is a continuation-in-part of application No. 08/956,448, filed on Oct. 23, 1997, now Pat. No. 5,987,359, which is a continuation of application No. 08/549,046, filed on Oct. 27, 1995, now Pat. No. 5,725,564.

(51) Int. Cl.
*A61N 1/00* (2006.01)
(52) U.S. Cl. .................................. 607/72; 607/152
(58) Field of Classification Search ............. 607/66, 607/72–74, 152
See application file for complete search history.

(56) References Cited

U.S. PATENT DOCUMENTS

| | | | |
|---|---|---|---|
| 3,805,769 A | 4/1974 | Sessions | |
| 3,911,906 A | 10/1975 | Reinhold, Jr. | |
| 3,993,049 A | 11/1976 | Kater | |
| 4,066,078 A | 1/1978 | Berg | |
| 4,777,954 A | 10/1988 | Keusch et al. | |
| 4,813,418 A * | 3/1989 | Harris | 607/156 |
| 4,860,754 A | 8/1989 | Sharik | |
| 4,895,154 A * | 1/1990 | Bartelt et al. | 607/50 |
| 4,926,878 A | 5/1990 | Snedeker | |
| 4,989,607 A | 2/1991 | Keusch et al. | |
| 5,406,945 A | 4/1995 | Riazzi et al. | |
| 5,427,096 A | 6/1995 | Bogusiewicz et al. | |
| 5,511,548 A | 4/1996 | Riazzi et al. | |
| 5,540,033 A | 7/1996 | Fox et al. | |
| 5,848,966 A | 12/1998 | Gusakov et al. | |
| 5,921,925 A | 7/1999 | Cartmell et al. | |
| 6,023,631 A | 2/2000 | Cartmell et al. | |
| 6,064,901 A | 5/2000 | Cartmell et al. | |
| 6,076,002 A | 6/2000 | Cartmell et al. | |
| 6,129,666 A | 10/2000 | DeLuca et al. | |
| 6,134,480 A | 10/2000 | Minogue | |
| 6,141,575 A * | 10/2000 | Price | 600/372 |
| 6,480,731 B1 | 11/2002 | DeLuca et al. | |
| 6,745,082 B2 * | 6/2004 | Axelgaard | 607/142 |

* cited by examiner

*Primary Examiner*—Scott M. Getzow
(74) *Attorney, Agent, or Firm*—Chambliss, Bahner & Stophel, P.C.

(57) ABSTRACT

A method for treating an oropharyngeal disorder in a patient by neuromuscular electrical stimulation includes selectively placing a plurality of electrodes in electrical contact with tissue of a pharyngeal region of the patient. The method also includes the steps of providing a pulse generator for generating a series of electrical pulses, each of which comprises a biphasic symmetrical waveform with an interval between the two phases, and attaching the plurality of electrodes to the pulse generator so that the series of electrical pulses may be provided to the patient through the plurality of electrodes. According to the method, a series of electrical pulses, each of which comprises a biphasic symmetrical waveform with an interval between the two phases, is generated, and said series of electrical pulses is provided to the patient through the plurality of electrodes. An apparatus for generating a series of electrical pulses for application of electrical neuromuscular stimulation to a patient through a plurality of electrodes for treatment of oropharyngeal disorders includes a pulse generator which generates a series of electrical pulses, each of which pulses comprises a biphasic symmetrical waveform with an interval between the two phases. The apparatus includes an intensity control circuit for regulating the series of electrical pulses such that the intensity of the electrical pulses does not exceed a predetermined value, a frequency controller for controlling the frequency at which the series of electrical pulses is generated so that such pulses are generated at a predetermined frequency, and a duration control circuit for controlling the duration of each such electrical pulse.

14 Claims, 12 Drawing Sheets

TREATMENT OF OROPHARYNGEAL DISORDERS BY APPLICATION OF NEUROMUSCULAR ELECTRICAL STIMULATION

RELATED APPLICATIONS

This application is a continuation-in-part of U.S. patent application Ser. No. 10/375,407, which was filed on Feb. 27, 2003, now U.S. Pat. No. 7,039,468 which is a continuation-in-part of U.S. application Ser. No. 10/308,105, filed Dec. 3, 2002 (now abandoned), which is a continuation of U.S. application Ser. No. 09/757,804, filed Jan. 11, 2001 (now abandoned), which is a continuation of U.S. application Ser. No. 09/236,829, filed Jan. 25, 1999 (now U.S. Pat. No. 6,198,970), which is a continuation-in-part of U.S. application Ser. No. 08/956,448, filed Oct. 23, 1997 (now U.S. Pat. No. 5,987,359), which is a continuation of U.S. application Ser. No. 08/549,046, filed Oct. 27, 1995 (now U.S. Pat. No. 5,725,564).

FIELD OF THE INVENTION

This invention relates to a method and apparatus for treating oropharyngeal disorders. In particular, the present invention relates to a method and apparatus for treating oropharyngeal disorders by providing neuromuscular electrical stimulation to a patient's pharyngeal region.

BACKGROUND OF THE INVENTION

Asymptomatic and symptomatic oropharyngeal disorders can lead to an inability to swallow or to difficulty in swallowing. These disorders may be caused, for example, by neurodegenerative diseases, strokes, brain tumors or respiratory disorders.

Swallowing is a complicated action whereby food is moved from the mouth through the pharynx and esophagus to the stomach. The act of swallowing may be initiated voluntarily or reflexively but is always completed reflexively. The act of swallowing occurs in three stages and requires the integrated action of the respiratory center and motor functions of multiple cranial nerves, and the coordination of the autonomic system within the esophagus. In the first stage, food or some other substance is placed on the surface of the tongue. The tip of the tongue is placed against the hard palate. Elevation of the larynx and backward movement of the tongue forces the food through the isthmus of the fauces in the pharynx. In the second stage, the food passes through the pharynx. This involves constriction of the walls of the pharynx, backward bending of the epiglottis, and an upward and forward movement of the larynx and trachea. Food is kept from entering the nasal cavity by elevation of the soft palate and from entering the larynx by closure of the glottis and backward inclination of the epiglottis. During this stage, respiratory movements are inhibited by reflex. In the third stage, food moves down the esophagus and into the stomach. This movement is accomplished by momentum from the second stage, peristaltic contractions, and gravity.

Although the main function of swallowing is the propulsion of food from the mouth into the stomach, swallowing also serves as a protective reflex for the upper respiratory tract by removing particles trapped in the nasopharynx and oropharynx, returning materials to the stomach that are refluxed into the pharynx, or removing particles propelled from the upper respiratory tract into the pharynx. Therefore, the absence of adequate swallowing reflex greatly increases the chance of pulmonary aspiration.

In the past, patients suffering from oropharyngeal disorders have been subjected to dietary changes or thermal stimulation treatment to regain adequate swallowing reflexes. Thermal stimulation involves immersing a mirror or probe in ice or another cold substance and stimulating the tonsillar fossa with the cold mirror or probe. Upon such stimulation, the patient is directed to close his mouth and attempt to swallow. While dietary changes and exercise rehabilitation using thermal stimulation may be effective for treating oropharyngeal disorders, some patients may require weeks or months of therapy. It is also difficult to distinguish patients who require such treatments from patients who recover spontaneously.

Muscle fibers are generally characterized as Type I or Type II, depending on their contraction rate, endurance, resistance to fatigue and other characteristics. Type I muscle fibers are characterized by slow contraction rates, high endurance, slowness to fatigue and low power. In contrast, Type II muscle fibers are characterized by fast contraction rates, low endurance, quickness to fatigue and high power. All muscles contain both types of fibers, and several of the muscles involved in swallowing contain a higher proportion of Type II fibers. It is believed that the high speed and dynamic and forceful action of the swallow are due to this preponderance of Type II fibers.

Most conditions treated in therapy are characterized by a degree of disuse atrophy. Disuse atrophy refers to changes in the muscle after a period of immobilization or reduced activity. The most obvious change is a decrease in the cross-sectional area of the muscle belly, with Type II fibers being affected to a greater degree than Type I fibers. Swallowing musculature shows these typical changes with disuse, but the impact on these muscles is relatively great since the overall percentage of Type II fibers is higher. During exercise rehabilitation, Type I fibers are contracted first, whereas the larger sized Type II fibers are involved only when the effort increases. Consequently, Type I fibers receive the most benefit from exercise rehabilitation. On the other hand, during electrical stimulation, Type II fibers are the first to contract, whereas Type I fibers contract only later when the pulse width and intensity are raised above a certain threshold. Consequently, electrical stimulation preferentially trains Type II fibers.

Neuromuscular electrical stimulation (NMES) has been used to alleviate pain and stimulate nerves, as well as a means for treating disorders of the spinal cord or peripheral nervous system. Neuromuscular electrical stimulation (as well as electrical muscle stimulation) has further been used to facilitate muscle reeducation and with other physical therapy treatments. In the past, neuromuscular electrical stimulation or electrical muscle stimulation were not indicated for use in the neck because of concerns that the patient could develop spasms of the laryngeal muscles, resulting in closure of the airway or difficulty in breathing, and/or because of concerns that the introduction of electrical current into the neck near the carotid body would cause bradycardia and consequent hypotension.

More recently, neuromuscular electrical stimulation has been used to stimulate the recurrent laryngeal nerve to stimulate the laryngeal muscles to control the opening of the vocal cords to overcome vocal cord paralysis, to assist with the assessment of vocal cord function, to aid with intubation, and other related uses. Generally, there have been no adverse reactions to such treatment techniques. However, neither neuromuscular electrical stimulation nor electrical muscle stimulation have been used in the treatment of oropharyngeal disorders to promote the swallowing reflex, which involves the integrated action of the respiratory center and motor functions of multiple cranial nerves.

It would be desirable if a simple, non-invasive method and device could be provided for treating oropharyngeal disorders and promoting swallowing in an effective manner within a relatively short treatment period.

ADVANTAGES OF THE INVENTION

Among the advantages of the invention is that it provides a simple, non-invasive method and apparatus for treating oropharyngeal disorders and promoting swallowing by providing electrical stimulus to the pharyngeal region of a human patient.

Additional advantages of this invention will become apparent from an examination of the drawings and the ensuing description.

EXPLANATION OF TECHNICAL TERMS

As used herein, the term "electrical muscle stimulation" refers to the use of electrical stimulation for direct muscle activation of denervated muscle fibers in the absence of peripheral innervation.

As used herein, the term "neuromuscular electrical stimulation" refers to the use of electrical stimulation for activation of muscles through stimulation of the intact peripheral motor nerves.

As used herein, the term "pharyngeal region" refers to the anterior portion of the neck bounded on the upper side by the mandible and on the lower side by the clavicles and the manubrium of the sternum.

SUMMARY OF THE INVENTION

The invention comprises a method for treating an oropharyngeal disorder in a patient by electrical neuromuscular stimulation. According to this method, a plurality of electrodes are selectively placed in electrical contact with tissue of a pharyngeal region of the patient, and a pulse generator is provided for generating a series of electrical pulses, each of which comprises a biphasic symmetrical waveform with an interval between the two phases. A plurality of electrodes are attached to the pulse generator so that the series of electrical pulses may be provided to the patient through the plurality of electrodes, and a series of electrical pulses, each of which comprises a biphasic symmetrical waveform with an interval between the two phases, is generated. The series of electrical pulses is provided or transmitted to the patient through the plurality of electrodes.

The invention also comprises an apparatus for generating a series of electrical pulses, each of which pulses comprises a biphasic symmetrical waveform with an interval between the two phases, for application of electrical neuromuscular stimulation to a patient through a plurality of electrodes for treatment of oropharyngeal disorders. The apparatus comprises a pulse generator which includes an intensity control circuit for regulating the series of electrical pulses such that the intensity of the electrical pulses does not exceed a predetermined value, a frequency controller for controlling the frequency at which the series of electrical pulses is generated so that such pulses are generated at a predetermined frequency, and a duration control circuit for controlling the duration of each such electrical pulse.

A preferred apparatus for treating oropharyngeal disorders according to the present invention also includes a first pair of electrodes and a second pair of electrodes. This preferred apparatus includes a first pulse generator that is adapted for generating a first series of electrical pulses (each of which comprises a biphasic symmetrical waveform with an interval between the two phases) for output through a first channel and the first pair of electrodes, and a second pulse generator that is adapted for generating a second series of electrical pulses (each of which comprises a biphasic symmetrical waveform with an interval between the two phases) for output through a second channel and the second pair of electrodes. The first pulse generator of this preferred embodiment also includes a first intensity control circuit for regulating the series of electrical pulses for output through the first channel such that the electrical current does not exceed a first predetermined value, and the second pulse generator includes a second intensity control circuit for regulating the series of electrical pulses for output through the second channel such that the electrical current does not exceed a second predetermined value. Each of the preferred pulse generators of this embodiment also includes a frequency controller for controlling the frequency at which the series of electrical pulses is generated by the pulse generator so that such pulses are generated at a predetermined frequency, and a duration control circuit for controlling the duration of each such electrical pulse.

In a preferred embodiment of the invention, each of the electrodes includes a snap eyelet, a conductive film and an adhesive and conductive gel layer. The snap eyelet has a first side and a second side, and the second side has a connector to which a lead wire may be attached. The conductive film is attached to the first side of the snap eyelet, and the adhesive and conductive gel layer is attached to the conductive film and adapted to be attached to the skin of the patient. The preferred embodiment of the invention also includes at least one adhesively backed tape overlay for securing the electrodes to the skin of the patient.

In order to facilitate an understanding of the invention, the preferred embodiments of the invention are illustrated in the drawings, and a detailed description thereof follows. It is not intended, however, that the invention be limited to the particular embodiments described or to use in connection with the apparatus illustrated herein. Various modifications and alternative embodiments such as would ordinarily occur to one skilled in the art to which the invention relates are also contemplated and included within the scope of the invention described and claimed herein.

BRIEF DESCRIPTION OF THE DRAWINGS

The presently preferred embodiments of the invention are illustrated in the accompanying drawings, in which like reference numerals represent like parts throughout, and in which.

DESCRIPTION OF THE PREFERRED EMBODIMENTS

Figure 1:
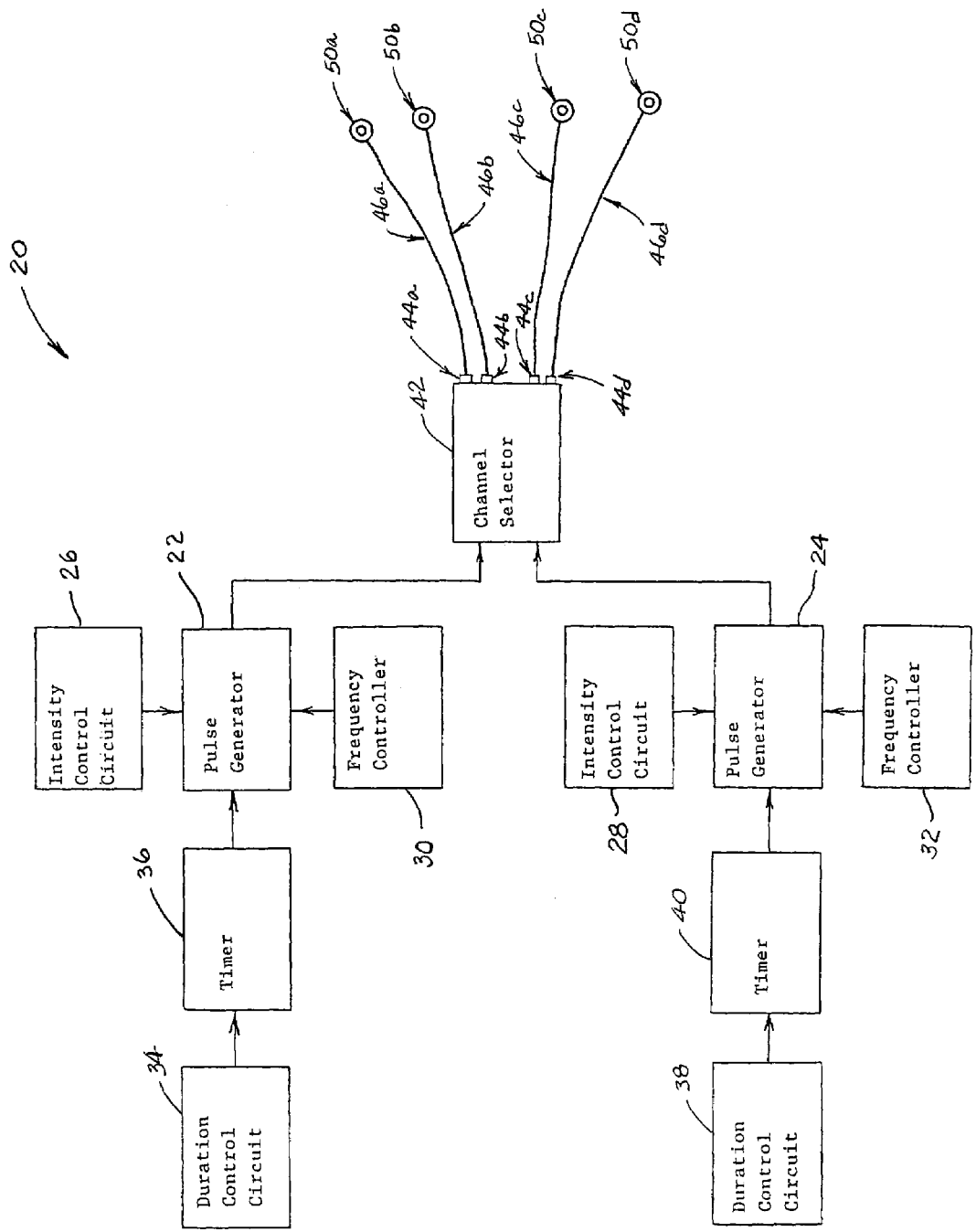
FIG. 1 is a schematic diagram of a preferred electrical neuromuscular stimulator according to the present invention for use in treating dysphagia and other oropharyngeal disorders.
Figure 6:
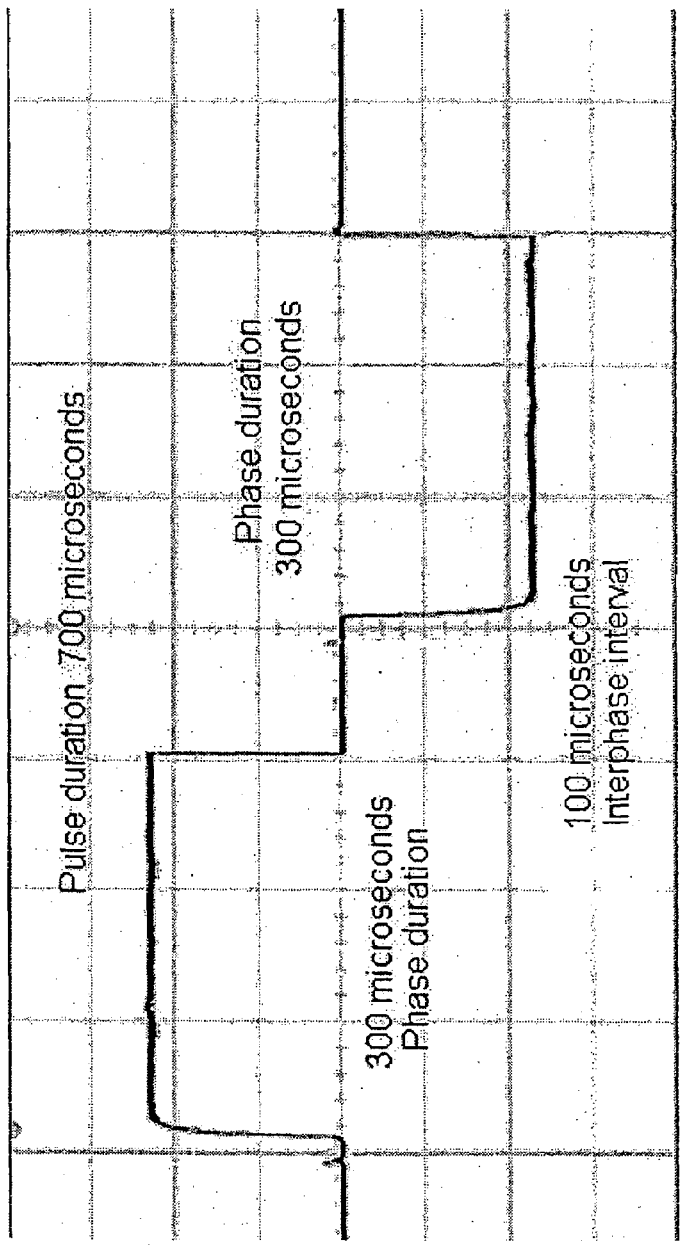
FIG. 6 is an illustration of a preferred waveform of an electrical pulse that is generated according to a preferred embodiment of the invention.

The present invention will now be described in detail with reference to the accompanying drawings, which are provided as illustrative examples of preferred embodiments of the invention only and not for purposes of limiting the same. FIG. 1 illustrates a preferred embodiment of an electrical neuromuscular stimulation apparatus or device 20 for use in providing neuromuscular electrical stimulation to the pharyngeal region of a patient in order to promote swallowing. As shown in FIG. 1, neuromuscular electrical stimulation device 20 includes a pulse generator, or more preferably, first pulse generator 22 and second pulse generator 24. A single pulse generator or more than two pulse generators may also be provided in the neuromuscular electrical stimulation device of this invention. Each such pulse generator is adapted to generate a series of electrical pulses, wherein each such pulse comprises a biphasic symmetrical waveform with an interval between the two phases. Preferably, each such pulse comprises a biphasic rectangular waveform having an interval between two phases of opposite polarity, such as is illustrated in FIG. 6.

Device 20 also includes one or more intensity control circuits for regulating the series of electrical pulses generated by each pulse generator such that the intensity of the electrical pulses does not exceed a predetermined value, such as for example, by regulating the series of electrical pulses so that the electrical current does not exceed 25 milliamps RMS. Preferably, an intensity control circuit is provided for each pulse generator. Thus, as shown in FIG. 1, intensity control circuit 26 is associated with first pulse generator 22 and intensity control circuit 28 is associated with second pulse generator 24. An intensity control circuit may also be provided to insure that the power of the electrical pulses generated by each pulse generator does not exceed a predetermined value and/or to insure that the voltage of the electrical pulses generated by each pulse generator does not exceed a predetermined voltage. In a preferred embodiment, the intensity control circuits 26 and 28 limit the current, power and/or voltage values of the electrical pulses output by pulse generators 22 and 24 using conventional limiter circuits. The predetermined current, power and/or voltage values may vary in accordance with the patient's physical condition and tolerances and the treatments performed. For example, in treatment of oropharyngeal disorders, the current applied should be sufficient to produce the desired response and promote the swallowing reflex. Generally, the intensity of the current, power and/or voltage outputs is determined in order to produce the desired response while providing the greatest comfort to the patient and minimizing as much as possible the amount of pin-prick sensation felt by the patient. However, the intensity of the pulses that are applied should not be so great as to pose any risk of laryngeal spasms or bradycardia in the patient. Good results have been obtained when pulse generators 22 and 24 are controlled by intensity control circuits 26 and 28 so as to generate a series of electrical pulses at a current of less than or equal to about 25 mA. The intensity of the current is typically begun at a level of about 0.5 mA and increased by small increments of preferably about 0.5 mA each until the swallow response or muscle fasciculation occurs.

The intensity control circuit may also comprise a voltage controller that may be employed to regulate the voltage of the electrical pulses generated by each pulse generator so that such voltage does not exceed a predetermined value, such as for example, about 100 V. The intensity control circuit may also comprise a power controller that may be employed to regulate the power of the electrical pulses generated by each pulse generator so that such power does not exceed a predetermined value, such as for example, about 2500 mW.

Preferred device 20 also includes a frequency controller for controlling the frequency at which the series of electrical pulses is generated by each pulse generator so that such pulses are generated at a predetermined frequency. Thus, as shown in FIG. 1, frequency controller 30 is associated with pulse generator 22 and frequency controller 32 is associated with pulse generator 24. The frequency controller modulates an electrical signal generated by the pulse generator at a predetermined frequency to produce the series of electrical pulses output by the pulse generator. The frequency controller may modulate the electrical signal at a fixed frequency, for example, 80 Hertz. In the alternative, the frequency controller may vary the frequency of the electrical pulses within a predetermined range of frequencies, for example, a range of frequencies from 30 to 100 Hertz, or it may permit an operator to set the frequency at a specific frequency within a predetermined range. Other frequency ranges as are known to those having ordinary skill in the art to which the invention relates may also be used. Generally, the frequency of the electrical pulses is selected in order to provide the desired response along with the greatest comfort to the patient and to minimize as much as possible the amount of pin-prick sensation felt by the patient.

Device 20 also includes a duration control circuit and an associated timer for controlling the duration (or pulse width) of each electrical pulse generated by a pulse generator. Thus, for example, duration control circuit 34 and timer 36 are associated with pulse generator 22 and duration control circuit 38 and timer 40 are associated with pulse generator 24. In a preferred embodiment of the invention, the pulse generator generates electrical pulses of a biphasic symmetrical waveform and the duration control circuit controls the total pulse duration of each such pulse to about 550 to about 850 microseconds, with an interphase interval of about 50 to about 150 microseconds. More preferably, as illustrated in FIG. 6, the duration control circuit controls the duration of each electrical pulse so that each such pulse has a total pulse duration of about 700 microseconds, comprised of a first phase duration of about 300 microseconds, an interphase interval of about 100 microseconds and a second (opposite polarity) phase duration of about 300 microseconds. Referring again to FIG. 1, the duration control circuits 34 and 38 may be adjusted manually or automatically using conventional timing circuits, such as timer 36 (for circuit 34) and timer 40 (for circuit 38).

In a preferred embodiment, the timers may also be employed to selectively control the amount of time during which electrical pulses are applied. Thus for example, the timers may be employed to apply electric pulses in each treatment cycle for a period within the range of 0.5 seconds to 30 seconds. Other durations as are known to those having ordinary skill in the art to which the invention relates may also be used. In the alternative, the treatment cycle time may be left in the control of the operator, so that electric pulses may be continuously generated and delivered to the electrodes until a satisfactory contraction of the swallowing musculature is achieved or the sensory tolerance level is reached in the patient. The timers may also be employed to control the time between treatment cycles, as well as the treatment time for a particular treatment session, or the total duration of time during which the pulse generators generate cycles of electric pulses, including the delay time between such cycles. For example, the timers may be set to provide a delay between treatment cycles ranging from 0.1 seconds to 60.0 seconds, or other suitable delay times. The treatment time for a particular treatment session may be set at any suitable period, such as fifteen, thirty, or sixty minutes, or the treatment time control function may allow for manually controlled continuous treatment. As with all settings, the particular values are highly specific to the application and patient. Furthermore, the timers may also control the amount of time required to reach the maximum intensity in each treatment session, such as for example, the time during which the intensity of the current is increased, by increments of about 0.5 mA (or other suitable increment), from an initial level of about 0.5 mA (or other suitable level) to a final level of about 25 mA (or other suitable level). Similarly, the timers may also control the amount of time required to decrease from the maximum intensity to zero intensity (or other suitable level, if desired) at the end of each treatment session.

In a preferred embodiment of the invention, a channel selector or switching network provides for activation of one or more electrodes or electrode arrays through which electrical pulses may be provided to a patient, using conventional switching circuits. Thus, for example, a channel selector may provide for the simultaneous activation of two electrode pairs through two pairs of output jacks. In the embodiment illustrated in FIG. 1, channel selector 42 may be employed to activate a first pair of jacks 44a and 44b and a second pair of jacks 44c and 44d. The electrical pulses from generator 22 may then be transmitted through channel selector 42, through jacks 44a and 44b to electrodes 50a and 50b through lead lines 46a and 46b respectively. Preferably, the current of the pulses transmitted through output jacks 44a and 44b may be regulated within the range of 0.5 to 25 milliamps in 0.5 milliamp increments. Similarly and independently, the current of the pulses generated by generator 24 may be transmitted through channel selector 42 to electrodes 50c and 50d through lead lines 46c and 46d respectively. Preferably, the current of the pulses transmitted through output jack 44c and 44d may be regulated within the range of 0.5 to 25 milliamps in 0.5 milliamp increments. It is contemplated within the scope of the invention that the current may be set at the same or different levels for output through the separate channels.

Figure 5:
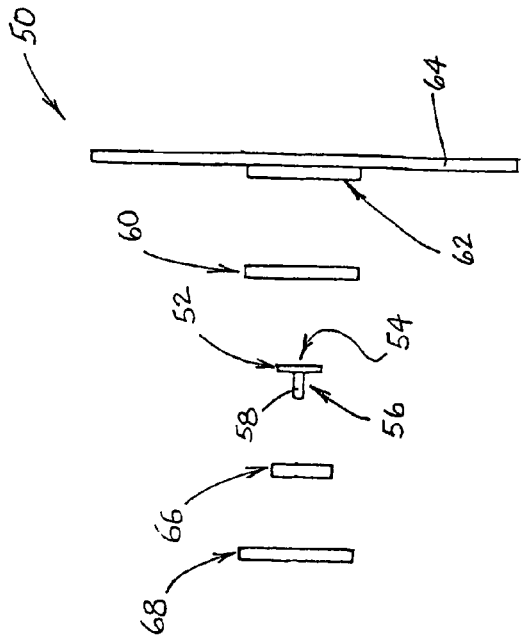
FIG. 5 is an exploded view of a preferred embodiment of an electrode of the invention.

As shown in FIG. 1, preferred device 20 includes two electrode pairs 50a and 50b, and 50c and 50d, although other electrode arrays may also be employed in connection with the invention. For human applications, the electrodes 50 are preferably snap electrodes having a construction such as is illustrated in FIG. 5 (described in more detail hereinafter). Preferably, as shown in the drawings, the electrodes in each pair are of equal size, so that neither is considered to be dispersive of the charge or current transmitted therethrough.

At least one lead wire is provided for each electrode. Each such lead wire has an electrode connection end for connection to an electrode and an output jack end for connection to the pulse generator (or for connection to the pulse generator through a channel selector). These connection ends may be of conventional design or any design that is suitable for connecting an electrode to an output jack of or associated with the pulse generator, as would be appreciated by those having ordinary skill in the art to which the invention relates. Thus, as shown in FIG. 1, lead wire 46a has an electrode connection end which is attached to electrode 50a and an output jack end that is attached to output jack 44a of channel selector 42. Similarly, lead wire 46b has an electrode connection end which is attached to electrode 50b and an output jack end that is attached to output jack 44b, and lead wire 46c has an electrode connection end which is attached to electrode 50c and an output jack end that is attached to output jack 44c, and lead wire 46d has an electrode connection end which is attached to electrode 50d and an output jack end that is attached to output jack 44d. Lead wires 46a, 46b, 46c and 46d may be made from any physiologically acceptable conductive metal, preferably insulated aluminum or copper wire. Multistrand wire is preferable to "wire wrap" type wire because multistrand wire is softer and less likely to break with repeated flexing.

Preferred electrode 50 is illustrated in some detail in FIG. 5. As shown therein, preferred electrode 50 comprises a metal snap eyelet 52 having a first side 54 and a second side 56. The first side of each preferred snap eyelet is generally circular and has a diameter of about 7 mm. The second side has a stud connector 58 to which a lead wire may be attached. The preferred electrode also includes a generally circular conductive film 60 having a diameter within the range of 16 mm-22 mm that is attached to the first side of the snap eyelet. Preferably, conductive films at the lower end of this size range, or dime-sized films, are used in electrodes intended for application to children, whereas films at the upper end of the preferred range, or nickel-sized films, are used in electrodes intended for application to adults. As used herein, the term "conductive film" refers to a thin substrate that is electrically conductive. Preferably, the film is a carbon film having a thickness of about 0.10 mm. However, other conductive substrates as are known to those having ordinary skill in the art to which the invention relates may also be employed. The preferred electrode also includes an adhesive and conductive gel layer 62, preferably of cross-linked hydrogel having a thickness of about 1.0 mm, that is attached to the conductive film and adapted to be attached to the skin of the patient. For application of the electrodes to children, hi-tack versions of the adhesive gel layer are preferred because of the relatively small skin-contact area. A suitable hi-tack conductive gel adhesive known as RG-72 is available from the Promeon Company. The preferred electrode also includes a release liner 64 that is attached to the gel layer to protect it prior to application to the skin of the patient. Preferably, the release liner is made of polyester or other suitable material having a thickness of about 0.125 mm. The electrode of the invention may also include a conductive bond tape layer 66, having a hole for the stud, that is adapted to more securely attach eyelet 52 to conductive film 60. An electrically-insulating layer 68 may also be provided to overlie the conductive bond tape layer, or if there is no such layer, the eyelet itself. The insulating layer will also include a hole through which the stud may protrude. Preferred results have been obtained when the maximum electrical impedance of the electrode is about 150 ohms.

A preferred embodiment of the invention, such as is illustrated in the drawings, is sold under the trademark "VitalStim" by the Chattanooga Group Division of Encore Medical LP, which is located in Chattanooga, Tenn. The "VitalStim" device includes a pair of pulse generators, each of which is adapted to generate a series of electrical pulses for transmission to a patient through a channel selector and a pair of electrodes. The pulses generated by each of the pulse generators of the "VitalStim" device are biphasic symmetrical rectangular waveforms having a total pulse duration of about 700 microseconds which includes an interphase interval of about 100 microseconds.

Figure 3:
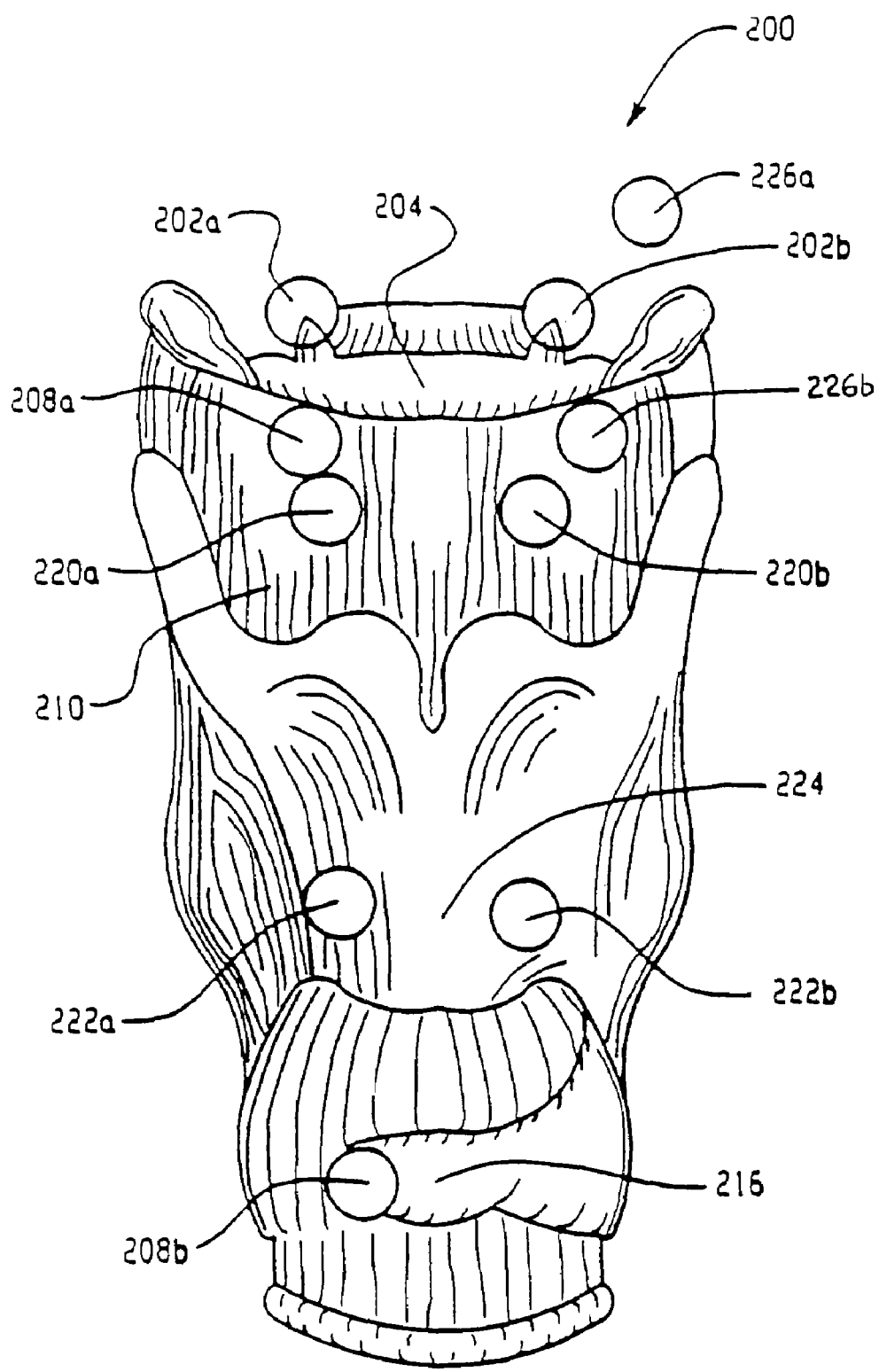
FIG. 3 is a view of a portion a pharyngeal region of a patient illustrating several exemplary placements of a pair of electrodes according to the present invention.
Figure 4:
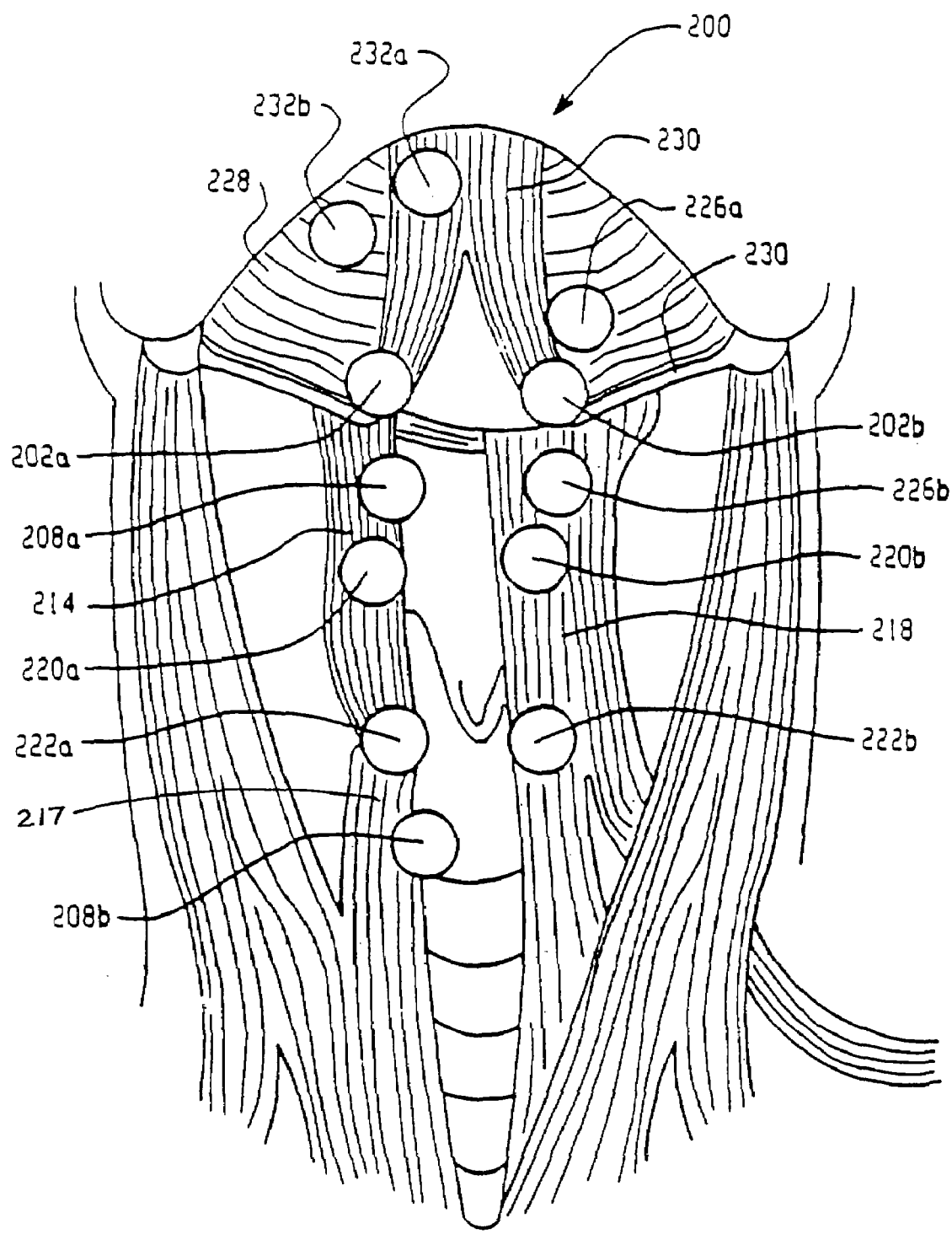
FIG. 4 is a view of a portion a pharyngeal region of a patient illustrating several exemplary placements of a pair of electrodes according to the present invention.

As shown in FIGS. 3 and 4, in a two-electrode embodiment of the present invention, a pair of electrodes 202*a* and 202*b* may be positioned on the skin of the pharyngeal region 200 at approximately the position of the lesser horns of the hyoid bone 204 on either side of the pharyngeal region 200 and just above the body of the hyoid bone. In this arrangement, the electrodes overlie the muscles of the floor of the mouth. In an alternative two-electrode embodiment of the present invention, a pair of electrodes 208*a* and 208*b* may be positioned on the side of the pharyngeal region 200 on one side of the midline of the pharyngeal region 200. In this embodiment of the invention, electrode 208*a* is placed on the thyrohyoid membrane 210 at approximately the level of the lesser horn of the hyoid bone 204, so as to overly the sternohyoid muscle and the thyrohyoid muscle 214, and electrode 208*b* is placed on the cricoid cartilage 216 to the side of the midline of the pharyngeal region 200, so as to overly the sternothyroid muscle 217 and the sternohyoid muscle on one side of the midline of the pharyngeal region. In yet another embodiment of the present invention, a pair of electrodes 220*a* and 220*b* may be positioned on the skin of the pharyngeal region 200 on the thyrohyoid membrane 210 on either side of the midline of the pharyngeal region 200. In this arrangement, these electrodes overlie the thyrohyoid muscle 214 and the sternohyoid muscle 218. In another embodiment of the present invention, a pair of electrodes 222*a* and 222*b* may be positioned on the skin of the pharyngeal region 200 on either side of the midline of the pharyngeal region 200 proximately midway between the thyroid notch 224 and the cricoid cartilage 216. In this arrangement, these electrodes overlie the sternohyoid muscle 218 and the transition zone between the sternothyroid muscle and the thyrohyoid muscle on either side of the midline of the pharyngeal region 200.

In an additional embodiment of the present invention, a pair of electrodes 226*a* and 226*b* may be positioned on the skin of the pharyngeal region 200 on one side of the midline of the pharyngeal region 200. In this embodiment, one electrode 226*a* is placed just lateral to the lesser horn of the hyoid bone 204 proximately midway between the hyoid bone 204 and the lower border of the mandible (not shown), so as to overly the mylohyoid muscle 228 and the digastric muscle 230. In this embodiment, the other electrode 226*b* is placed proximate to the upper end of the thyrohyoid membrane 210 and proximate to the hyoid bone 204 or on the hyoid bone 204 proximately at the level of the lesser horn of the hyoid bone 204, so as to overly the sternohyoid muscle 218 and the thyrohyoid muscle. In yet another embodiment of the present invention (FIG. 4), a pair of electrodes 232*a* and 232*b* may be positioned on the skin of the pharyngeal region 200 to the side of the midline of the pharyngeal region 200. In this arrangement, one electrode 232*a* is placed on the midline of the pharyngeal region near the chin (not shown), and the other electrode 232*b* is placed laterally to the other electrode. These electrodes overlie the mylohyoid muscle 228 and the digastric muscle 230 in the midline and to one side of the midline of the pharyngeal region 200. In general, the placement and sizes of the electrodes are selected in accordance with the present invention so as to avoid the carotid body and to insure the safety of the patient.

Figure 8:
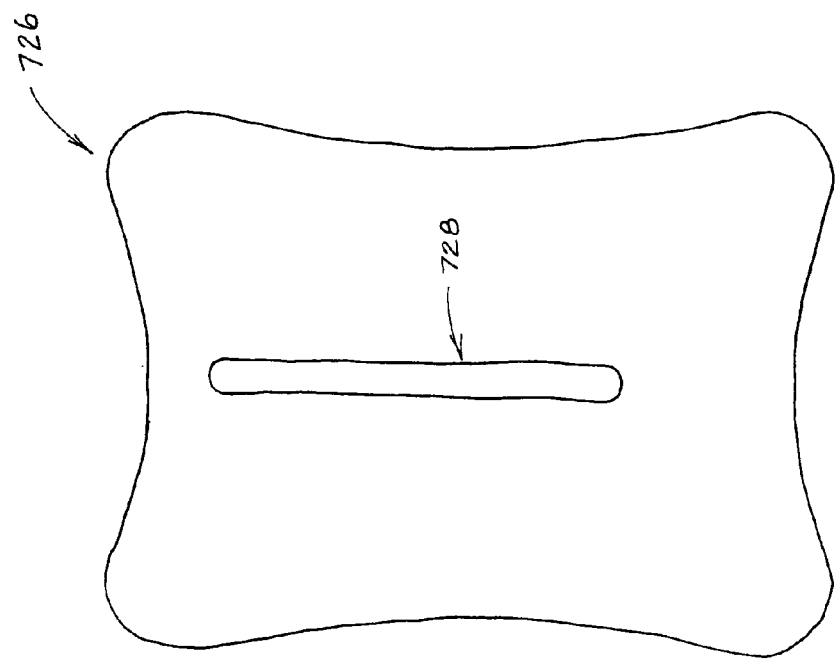
FIG. 8 is a front view of a preferred adhesively backed tape overlay for use in securing electrodes to the skin of a patient according to the invention.
Figure 7:
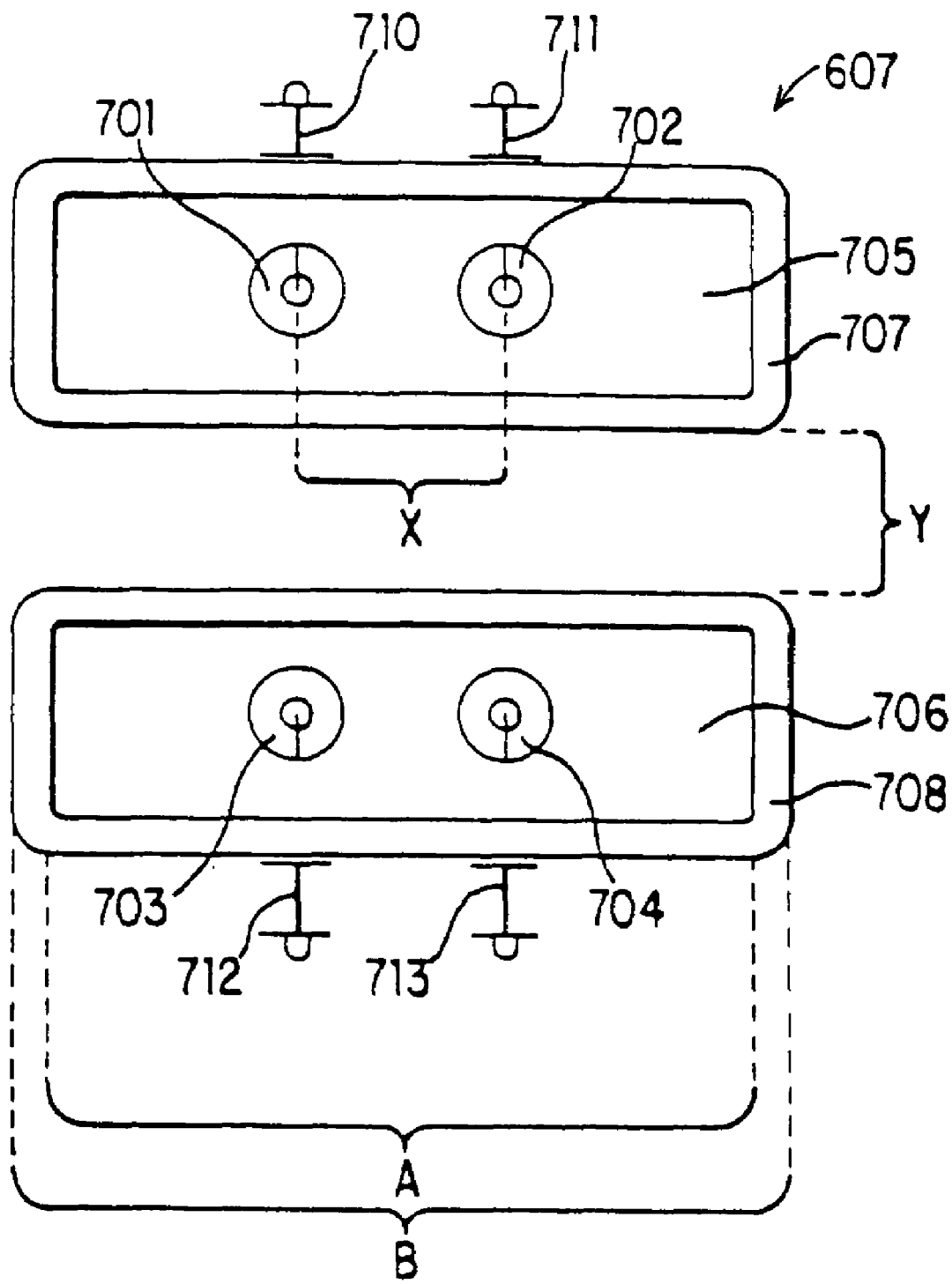
FIG. 7 is a diagram of a first embodiment of a first embodiment of an electrode array that may be used in connection with (or as a part of) the invention.
Figure 7A:
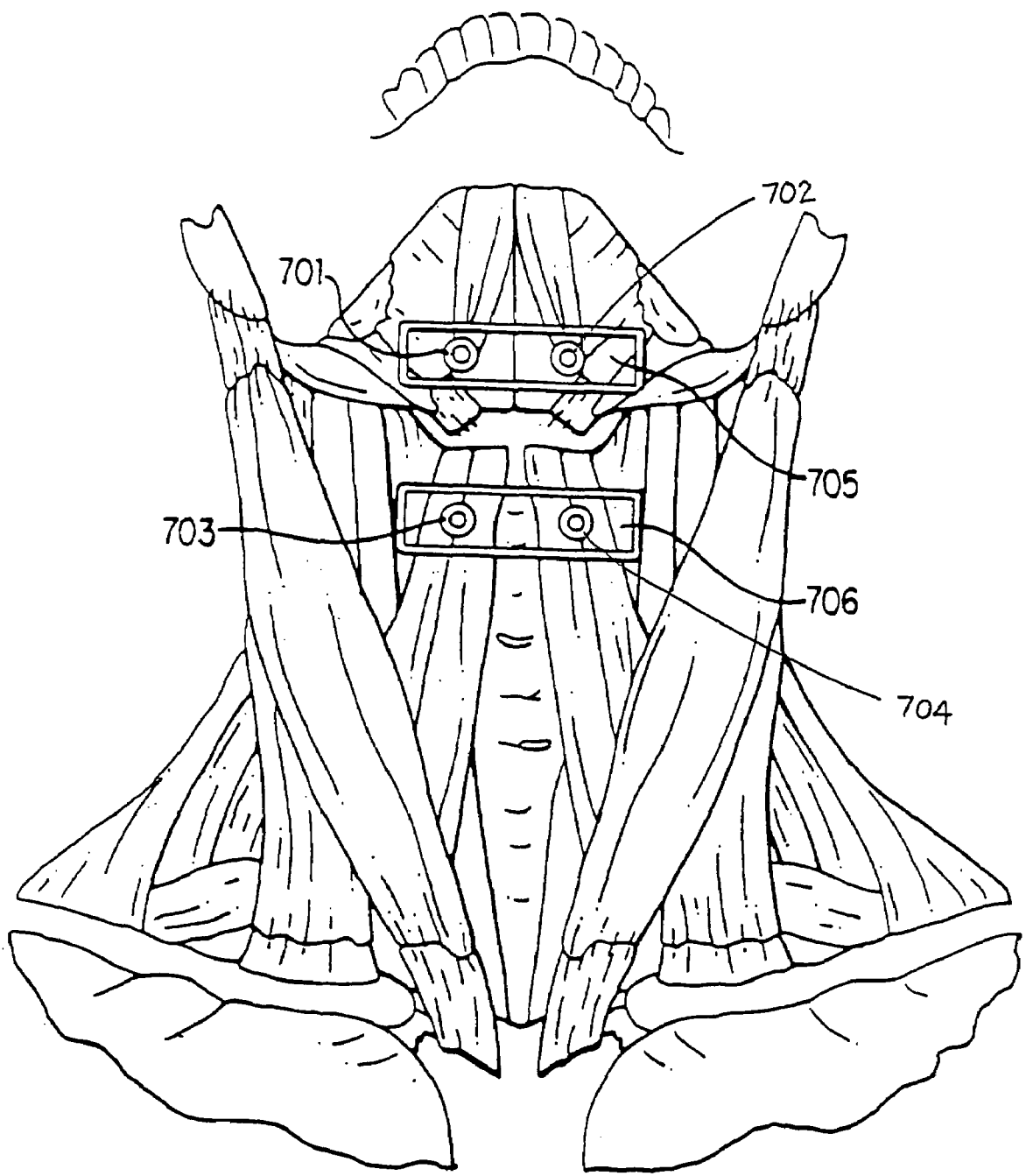
FIG. 7A illustrates the placement of the electrode array of FIG. 7 on the pharyngeal region of a human patient.

An embodiment of an electrode array that is suitable for use in conjunction with electrical stimulation device 20 for treatment of oropharyngeal disorders is illustrated in FIG. 7. Each electrode in array 607 stimulates one or more pharyngeal muscles with electrical stimulation provided by a pulse generator of device 20. The arrangement of electrodes and connecting wires shown in FIG. 7 is provided as an example and is not intended to limit the scope of the present invention. Also, multiple electrodes, including square arrays of four, sixteen, twenty-five, or thirty-six electrodes or more, or vertically arranged pairs of two or four electrodes may be used. As the number of electrodes increases, the surface area treated by the electrode array may be increased and/or the electrodes may be more closely positioned. As shown in FIG. 7, array 607 preferably comprises four electrodes 701, 702, 703 and 704, which are positioned on the tissue of the pharyngeal region of a patient using adhesive bands 705 and 706 as illustrated in FIG. 7A, or more preferably, with a pair of adhesively backed tape overlays such as are illustrated in FIG. 8 (and described hereinafter in more detail). The adhesive bands illustrated in FIGS. 7 and 7A for attachment of each pair of electrodes in array 607 to the patient may have a width of approximately eight centimeters, shown as distance "A" in FIG. 7. Contact pads 707 and 708 having a width of approximately eight and a half centimeters (shown as distance "B" in FIG. 7) are also provided. In the embodiment of the invention illustrated in FIGS. 7 and 7A, the electrodes are preferably arranged in two vertical pairs, each pair on one lateral side (e.g., the right hand or left hand side) of the pharyngeal region of the patient, with one electrode positioned above the patient's Adams Apple and the other below the Adams Apple of the patient. The first pair of electrodes, 701 and 703, is positioned on the patient's left side (the right side of FIGS. 7 and 7A). The second pair of electrodes, 702 and 704, is positioned in the same arrangement on the opposite side of the patient's pharyngeal region. Each pair of electrodes may preferably be positioned such that the distance between the centers of the electrodes in each pair, shown as distance "X" in FIG. 7, may be approximately three to four centimeters or other spacing as required to position the electrodes on the pharyngeal region of the patient as described above. The electrodes of each pair may preferably be spaced at a distance, shown as distance "Y" in FIG. 7, of approximately two and a half centimeters or other spacing as required to position the electrodes on the pharyngeal region of the patient as described above. In the two-pair electrode arrangement described above, the two electrodes 701 and 703 that are positioned on one lateral side (e.g., right or left side) of the patient's pharyngeal region are coupled to a first output channel of the device 20, and the two electrodes 702 and 704 that are positioned on the other lateral side of the patient's pharyngeal region are coupled to a second output channel of the device. In the embodiment of FIGS. 7 and 7A, electrodes 701, 703, 702 and 704 of electrode array 607 may each be independently coupled to an output jack (44a, 44b, 44c and 44d, respectively) of channel selector 42 by lead wires 710, 711, 712, and 713 respectively. As a result, each electrode pair independently receives one or more series of electrical pulses generated by one of pulse generators 22 or 24. It is also contemplated that each electrode (rather than each electrode pair) in this arrangement of electrodes may independently receive one or more series of electrical pulses generated by a pulse generator.

Figure 7B:
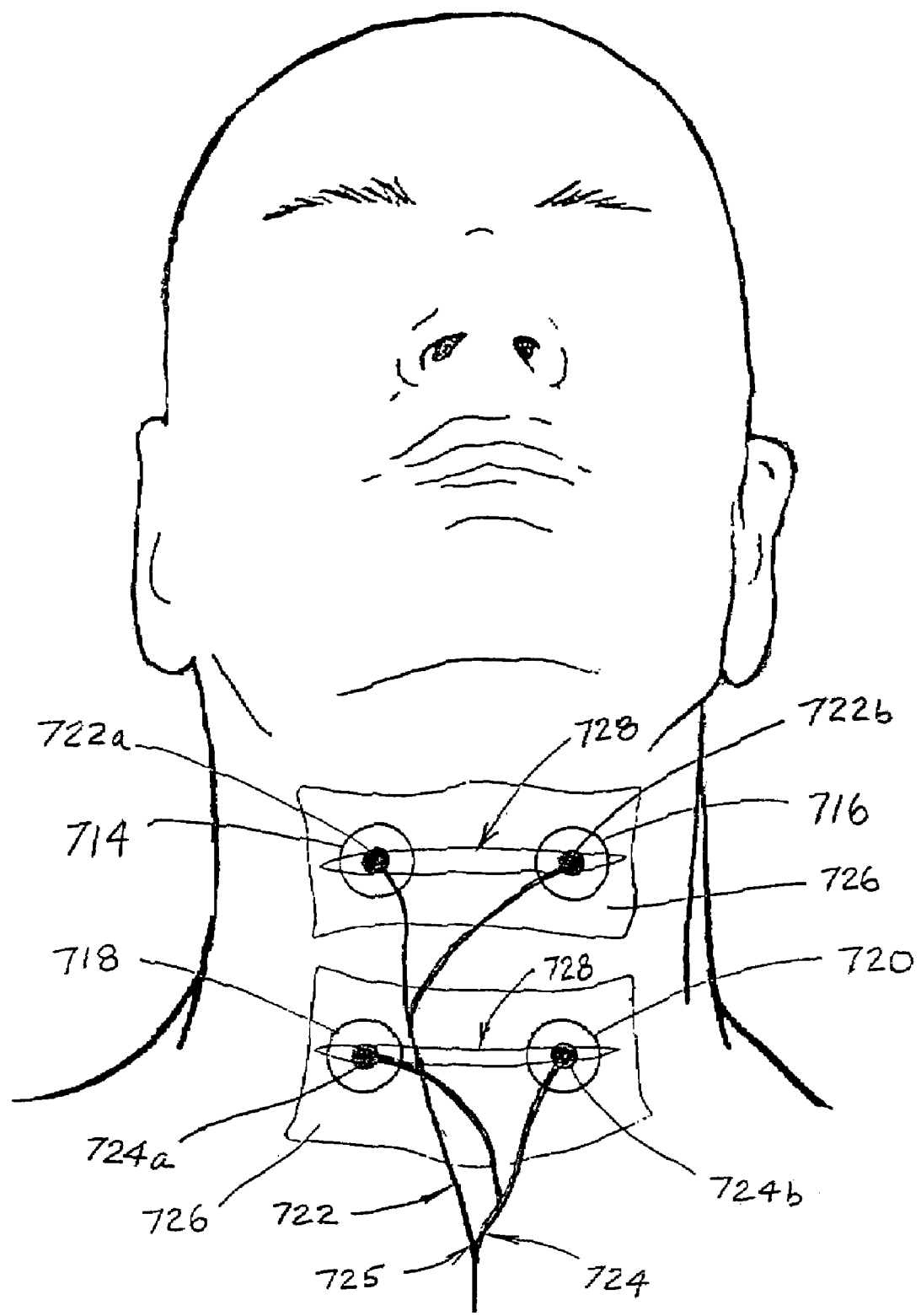
FIG. 7B illustrates the placement on the throat of a patient of a second embodiment of an electrode array that may be used in connection with (or as a part of) the invention.

Another arrangement of electrodes, in two horizontal pairs, is illustrated in FIG. 7B. As shown therein, a first pair of electrodes 714 and 716 are placed horizontally immediately above the thyroid notch. A second pair of electrodes 718 and 720 are placed horizontally below the notch. Preferably, the first pair of electrodes of this array is independently coupled, through a pair of output jacks, (not shown in FIG. 7B) to channel selector 42 of device 20 (shown in FIG. 1) by lead wire 722, comprised of a pair of electrode connection ends 722a and 722b and a pair of output jack ends (not shown). In similar fashion, the second pair of electrodes of this array is preferably independently coupled, through a pair of output jacks, (not shown in FIG. 7B) to channel selector 42 of device 20 by lead wire 724, comprised of a pair of electrode connection ends 724a and 724b and a pair of output jack ends (not shown). As a result, each of these pairs of electrodes independently receives one or more series of electrical pulses generated by one of the pulse generators of device 20. It is also contemplated that each electrode (rather than each electrode pair) of this arrangement of electrodes may independently receive one or more series of electrical pulses generated by a pulse generator. As shown in FIG. 7B, lead wires 722 and 724 may be mechanically joined together for ease in handling at junction 725.

In this embodiment of the invention, a pair of adhesively backed tape overlays 726 are provided to secure the electrodes to the skin of the patient. Tape overlay 726 (also shown in FIGS. 7C, 7D, 7E and 8) is preferably provided with a shape that will allow it to conform closely to the skin of the patient's neck in either the horizontal orientation shown in FIGS. 7B and 7C or the vertical orientation shown in FIGS. 7D and 7E. Tape overlay 726 is also preferably provided with an outer surface that does not absorb moisture and a centrally located slot 728 that may be aligned over the connectors of the snap eyelets for the preferred electrodes (shown in FIG. 5). This slot permits the electrodes to be placed on the skin of the patient's neck and secured with the tape overlay before connection the lead wires to the electrodes. The arrangement of electrodes illustrated in FIG. 7B is suitable for most laryngeal and pharyngeal motor defects. A similar arrangement (not shown) in which the first pair of electrodes 714 and 716 are placed slightly higher on the throat may be employed if it is desired to stimulate the tongue and upper pharyngeal muscles to promote swallowing.

Figure 7C:
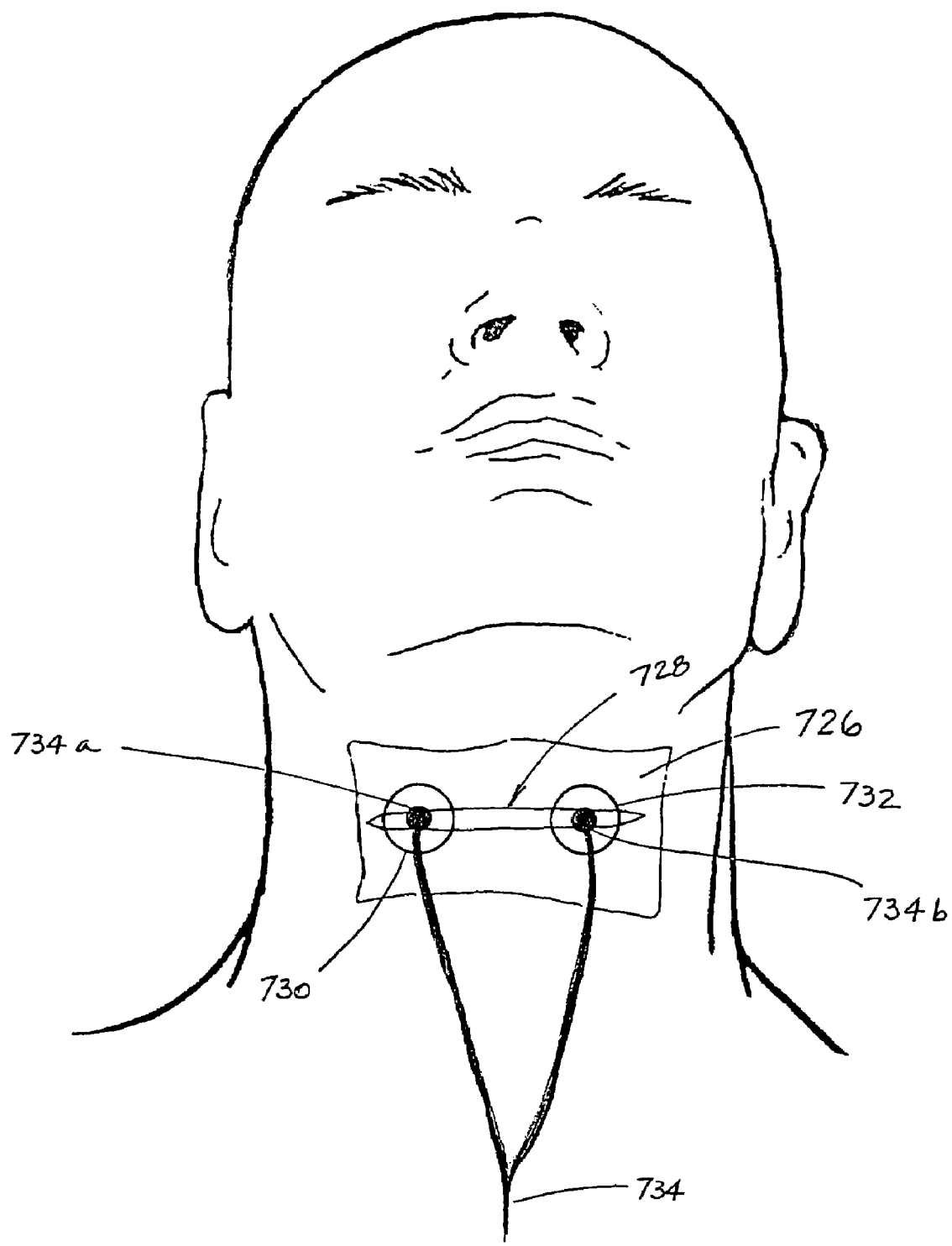
FIG. 7C illustrates the placement of a third embodiment of an electrode array on the throat of a patient according to a preferred embodiment of the invention.

Another arrangement of electrodes, in a single horizontally disposed pair, is illustrated in FIG. 7C. This arrangement is also suitable for treatment of most laryngeal and pharyngeal motor defects. As shown in FIG. 7C, electrodes 730 and 732 are placed horizontally immediately above the thyroid notch. This pair of electrodes is preferably independently coupled, through a pair of output jacks, (not shown in FIG. 7C) to channel selector 42 of device 20 by lead wire 734, comprised of a pair of electrode connection ends 734a and 734b and a pair of output jack ends (not shown). As a result, this pair of electrodes independently receives one or more series of electrical pulses generated by one of the pulse generators of device 20. It is also contemplated that each electrode (rather than each electrode pair) in this arrangement of electrodes may independently receive one or more series of electrical pulses generated by a pulse generator. Also as shown in FIG. 7C, an adhesively backed tape overlay 726 having a central slot 728 is provided to secure the electrodes to the skin of the patient.

Figure 7D:
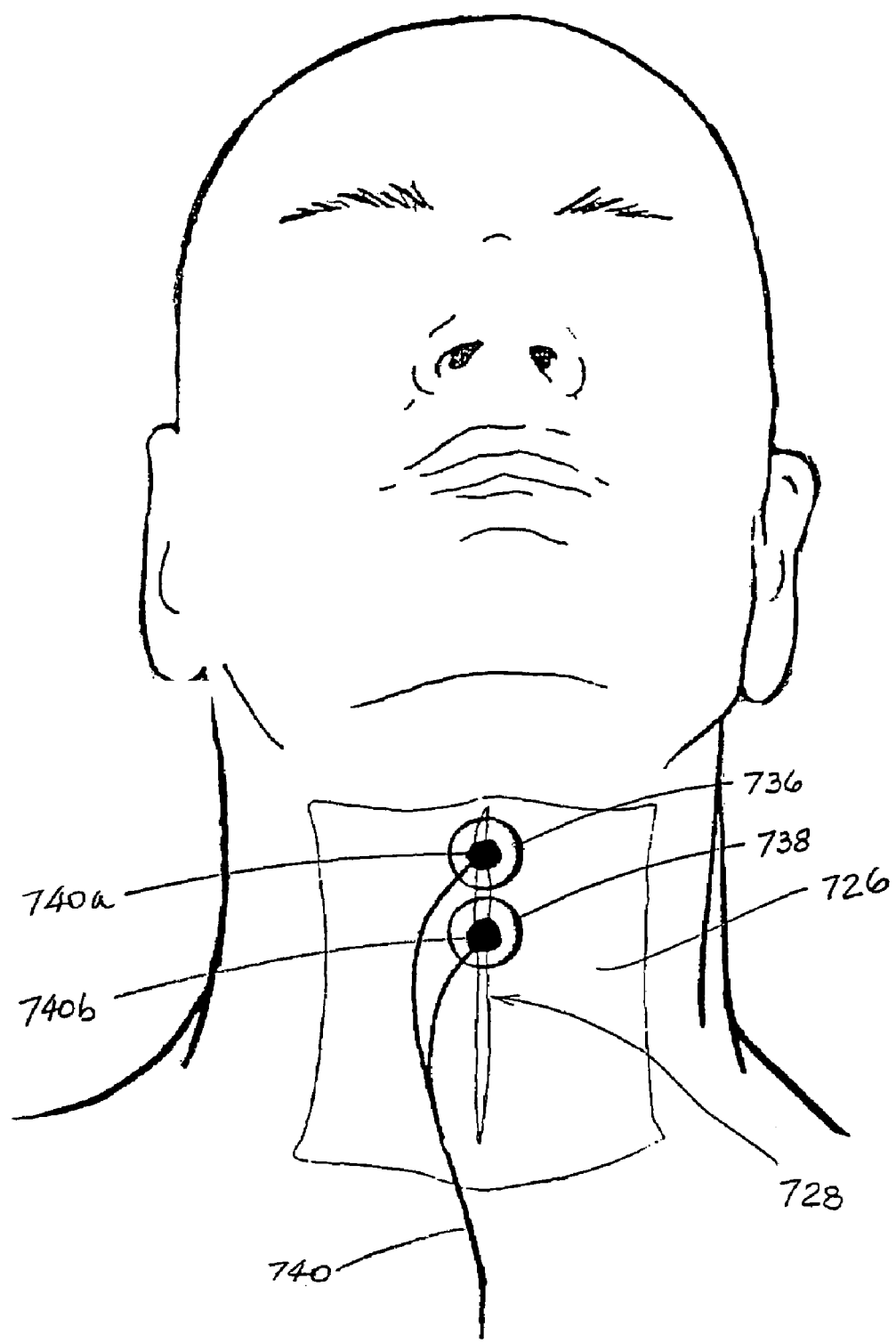
FIG. 7D illustrates the placement of a fourth embodiment of an electrode array on the throat of a patient according to a preferred embodiment of the invention.

FIG. 7D illustrates another arrangement of electrodes that is suitable for treatment of most laryngeal and pharyngeal motor defects. As shown therein, electrodes 736 and 738 are both placed above the thyroid notch in a vertical arrangement, generally on the centerline of the throat. This pair of electrodes is preferably independently coupled, through a pair of output jacks, (not shown in FIG. 7D) to channel selector 42 of device 20 by lead wire 740, comprised of a pair of electrode connection ends 740a and 740b and a pair of output jack ends (not shown). As a result, this pair of electrodes independently receives one or more series of electrical pulses generated by one of the pulse generators of device 20. It is also contemplated that each electrode (rather than each electrode pair) of this arrangement of electrodes may independently receive one or more series of electrical pulses generated by a pulse generator. Also as shown in FIG. 7D, an adhesively backed tape overlay 726 having a central slot 728 is provided to secure the electrodes to the skin of the patient.

Figure 7E:
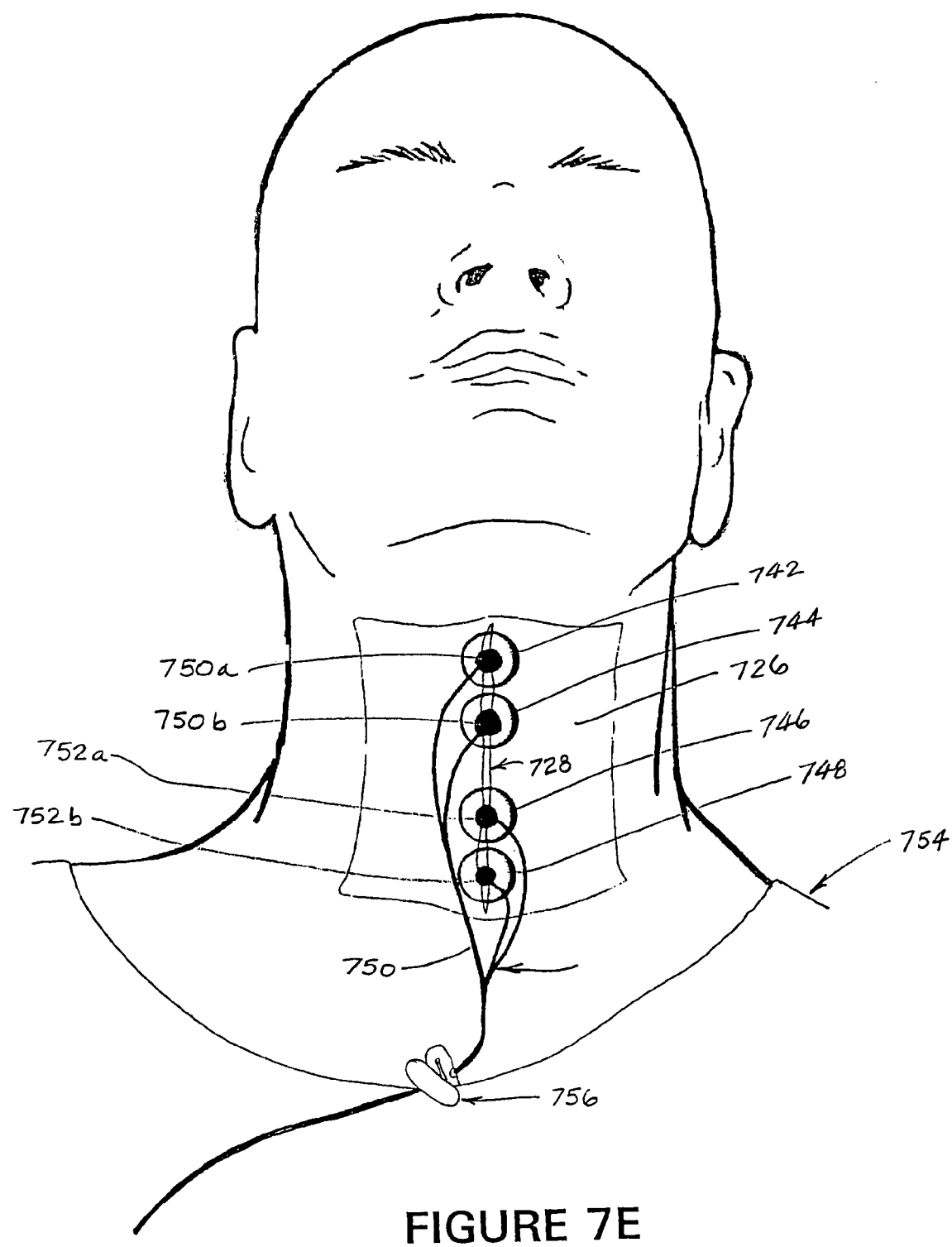
FIG. 7E illustrates the placement of a fifth embodiment of an electrode array on the throat of a patient according to a preferred embodiment of the invention.

FIG. 7E illustrates another arrangement of electrodes, in two pairs of vertically disposed electrodes. This arrangement is suitable for treatment of most laryngeal and pharyngeal motor defects and preferred for treatment of many such defects. In this arrangement, the four electrodes are positioned in a vertical row directly adjacent to one another, but not overlapping, starting with a first uppermost electrode being positioned on the patient's digastric muscles, covering the hyoid and the strap muscles of the patient's larynx, and ending with a fourth lowermost electrode being positioned at the base of the patient's thyroid cartilage. As shown in FIG. 7E, a first pair of electrodes 742 and 744 are placed vertically above the thyroid notch and generally along the centerline of the patient's throat. A second pair of electrodes 746 and 748 are placed vertically below the notch and generally along the same centerline as the first pair. The first pair of electrodes of this array is preferably independently coupled through a pair of output jacks, (not shown in FIG. 7D) to channel selector 42 of device 20 by lead wire 750, comprised of a pair of electrode connection ends 750a and 750b and a pair of output jack ends (not shown). The second pair of electrodes of this array is preferably independently coupled through a pair of output jacks, (not shown in FIG. 7D) to channel selector 42 of device 20 by lead wire 752, comprised of a pair of electrode connection ends 752a and 752b and a pair of output jack ends (not shown). As a result, each of these pairs of electrodes independently receives one or more series of electrical pulses generated by one of the pulse generators of device 20, although it is also contemplated that each electrode (rather than each electrode pair) in this arrangement may independently receive one or more series of electrical pulses generated by a pulse generator. The two upper electrodes 742 and 744 may be coupled to a first output channel of the channel selector 42, and the two lower electrodes 746 and 748 may be coupled to a second output channel of the channel selector. As shown in FIG. 7D, an adhesively backed tape overlay 726 is provided to secure the electrodes to the skin of the patient. In addition, lead wires 750 and 752 may be mechanically joined together for ease in handling, and clipped to patient's shirt 754 using preferred clip 756.

Figure 9:
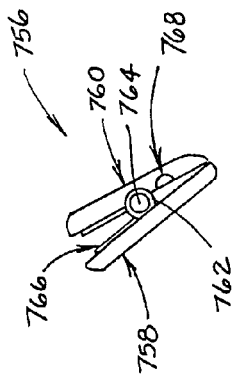
FIG. 9 is a side view of a preferred clip that forms a part of a preferred embodiment of the invention.

As shown in more detail in FIG. 9, clip 756 is comprised of first clip portion 758 and second clip portion 760. The first clip portion has an integral ring 762 in which pin 764 of the second clip portion may rotate. Spring 766 is provided between the clip portions to keep the clip "closed", yet allow it to be easily opened. A lead wire slot 768 is provided in clip portion 760 to retain the lead wire so that it may be clipped to an item of the clothing of the patient and thereby retained securely in place.

The electrode arrangements of FIGS. 7A-7E are provided as examples of electrode placement and are not intended to limit the number and arrangement of electrodes for use in practicing the present invention. The electrodes are selectively placed in any suitable site within the pharyngeal region 200 of the patient as shown in FIGS. 3 and 4. The placement of the electrodes in the pharyngeal region of the patient is based on several factors, such as the extent and type of oropharyngeal disorder exhibited by the patient and, given the extent and type of oropharyngeal disorder exhibited, those locations within the pharyngeal region, that when subjected to electrical stimulus, have the possibility of eliciting the strongest and most complete swallow. An evaluation for swallowing ability is done on the patient to determine the extent and type of oropharyngeal disorder. The critical elements in the evaluation are analysis by video fluoroscopy and clinical evaluation to determine the presence of a gag reflex, a dry swallow, and ability to tolerate one's own secretions. The placement of the electrodes may be changed several times in an effort to obtain the strongest and most effective treatment.

Figure 2:
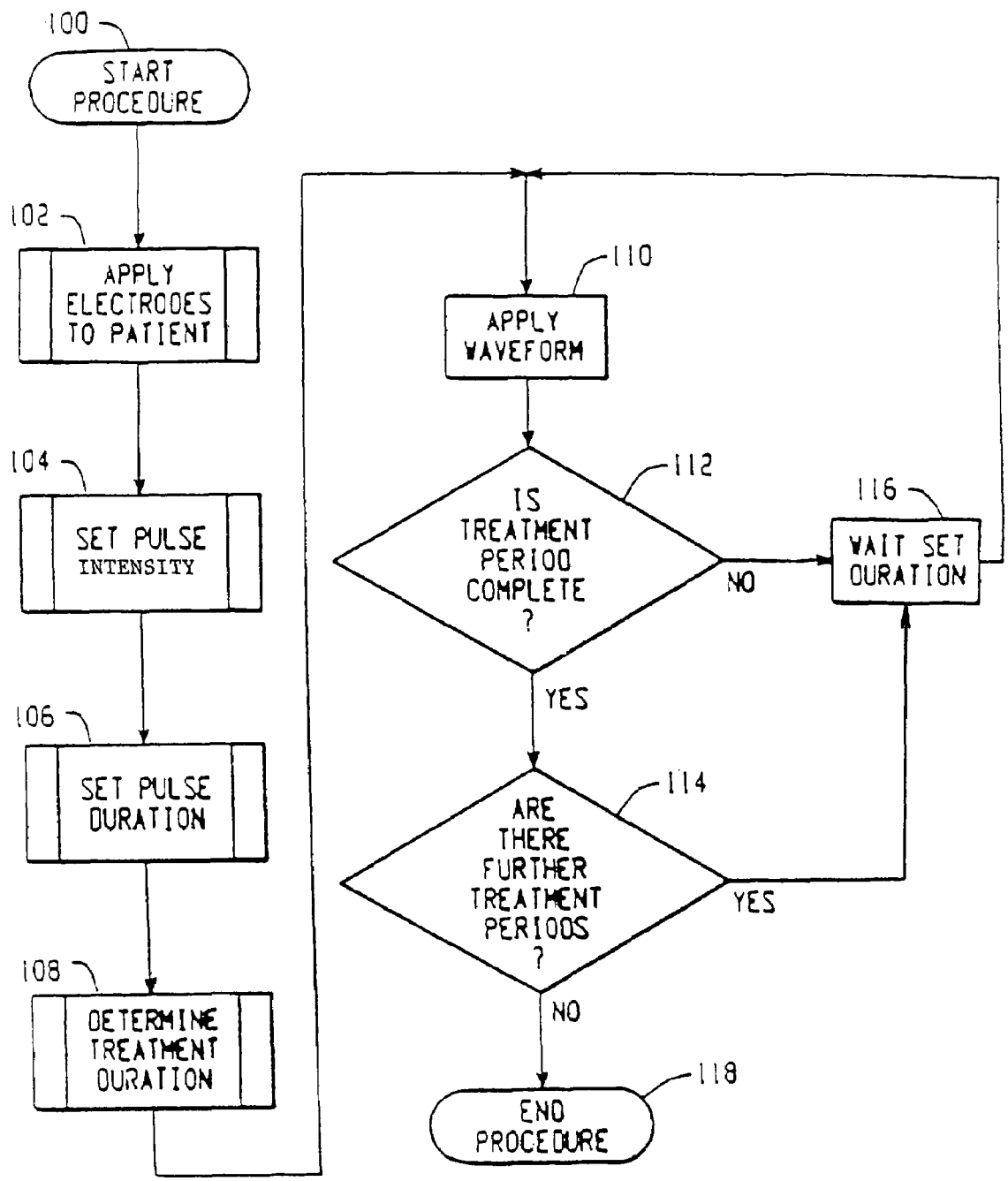
FIG. 2 is a flow chart of a preferred method for electrical pharyngeal neuromuscular stimulation according to the present invention for promoting swallowing.

A preferred method for neuromuscular electrical stimulation of the pharyngeal region according to the invention, using an apparatus similar to that shown in FIG. 1, will now be described with reference to FIG. 2. At step 100 (Start Procedure), the procedure for treating oropharyngeal disorders with neuromuscular electrical stimulation is initiated. Next, at step 102 (Apply Electrodes to Patient), electrodes are applied to the pharyngeal area of a patient, as described hereinabove. At step 104 (Set Pulse Intensity), the desired intensity of the electrical pulses is set, preferably at a current level of less than or equal to about 25 mA. Similarly, at step 106 (Set Pulse Duration), the duration of each pulse is set, so that each such pulse has a total pulse duration preferably within the range of about 550 to about 850 microseconds, with an interphase interval of about 50 to about 150 microseconds. Alternatively, the pulse duration may be fixed at a particular duration, such as is employed in the VitalStim device, for example, at a total pulse duration of about 700 microseconds, comprised of a first phase of about 300 microseconds, an interphase interval of about 100 microseconds, and a second phase of about 300 microseconds. At step 106, the interval between pulses may also be set, as well as the rate at which the intensity of the electrical pulses is raised from an initial level to a final treatment level during a treatment session. Finally, at step 108 (Determine Treatment Duration), a determination of the time of a treatment period (or the period during which electrical pulses are applied in one treatment session) is made. At step 110 (Apply Waveform), a series of electrical pulses, each of which comprises a biphasic symmetrical waveform with an interval between the two phases, is provided to the patient. Next, at step 112 (Is Treatment Period Complete?), a determination is made as to whether a treatment session is complete in accordance with the pre-selected treatment period duration. If the treatment period is complete, the next step in the preferred method is step 114 (Are There Further Treatment Periods?). It may be the case that two or more treatment sessions or periods have been set, with a predetermined rest interval in between the two periods. If at step 112, the determination is made that the treatment period has not been completed, or if at step 114, additional treatment periods have been set, the sequence progresses to step 116 ("Wait Set Duration"). After the set duration for any rest interval has elapsed, the sequence returns to step 110, whereupon electrical pulses will again be applied to the patient. If at step 112, the determination is made that the treatment period has been completed, and if no further treatments have been set, the final step in the preferred method is step 118 ("End Procedure").

The method and apparatus for neuromuscular electrical stimulation of the present invention provides an effective and non-invasive treatment for oropharyngeal disorders such as dysphagia. The method and apparatus for neuromuscular electrical stimulation is more effective for treating oropharyngeal disorders than traditional treatment methods, such as thermal stimulation-induced exercise rehabilitation. Further, the method and apparatus of the present invention is effective for treating worst-case dysphagia resulting from neurodegeneration and strokes.

Although this description contains many specifics, these should not be construed as limiting the scope of the invention but as merely providing illustrations of some of the presently preferred embodiments thereof, as well as the best mode contemplated by the inventor of carrying out the invention. The invention, as described herein, is susceptible to various modifications and adaptations, and the same are intended to be comprehended within the meaning and range of equivalents of the appended claims.

What is claimed is:

1. A method for treating an oropharyngeal disorder in a patient by neuromuscular electrical stimulation, said method comprising the steps of:
   (a) selectively placing a plurality of electrodes in electrical contact with tissue of a pharyngeal region of the patient;
   (b) providing a pulse generator for generating a series of electrical pulses, each of which comprises a biphasic symmetrical waveform with an interval between the two phases;
   (c) attaching the plurality of electrodes to the pulse generator so that the series of electrical pulses may be provided to the patient through the plurality of electrodes;
   (d) generating a series of electrical pulses, each of which comprises a biphasic symmetrical waveform with an interval between the two phases;
   (e) providing said series of electrical pulses to the patient through the plurality of electrodes.

2. The method of claim 1 which includes generating a series of electrical pulses at a current of less than or equal to about 25 mA.

3. The method of claim 1 which includes generating a series of electrical pulses at a frequency of about 80 Hz.

4. The method of claim 1 which includes generating a series of electrical pulses at a voltage of less than or equal to about 100 V.

5. The method of claim 1 which includes generating a series of electrical pulses at a power level of less than or equal to about 2500 mW.

6. The method of claim 1 which includes the following steps instead of step (a) of claim 1:
   (a1) providing a first electrode and a second electrode, each of which comprises:
       (i) a snap eyelet having a first side and a second side, said second side having a connector to which a lead wire may be attached;
       (ii) a conductive film that is attached to the first side of the snap eyelet;
       (iii) an adhesive and conductive gel layer that is attached to the conductive film and adapted to be attached to the skin of the patient;
   (a2) providing at least one adhesively backed tape overlay for securing the first and second electrodes to the skin of the patient;
   (a3) placing the first electrode on the skin of the patient's pharyngeal region with the adhesive gel layer in contact with the skin;
   (a4) placing the second electrode on the skin of the patient's pharyngeal region with the adhesive gel layer in contact with the skin;
   (a5) securing the electrodes to the skin of the patient's pharyngeal region by application of at least one adhesively backed tape overlay to the skin of the patient's pharyngeal region over at least a portion of each of the electrodes.

7. The method of claim 1 which includes generating a series of electrical pulses, each of which comprises a biphasic symmetrical rectangular waveform having a total pulse duration of about 550 to about 850 microseconds, which pulse duration includes an interphase interval of about 50 to about 150 microseconds.

8. The method of claim 1 which includes generating a series of electrical pulses, each of which comprises a biphasic symmetrical rectangular waveform having a total pulse duration of about 700 microseconds, which pulse duration includes a first phase of about 300 microseconds, an interphase interval of about 100 microseconds and a second phase of about 300 microseconds.

9. A method for treating an oropharyngeal disorder in a patient by neuromuscular electrical stimulation, said method comprising the steps of:
   (a) selectively placing a first pair of electrodes in electrical contact with tissue of a pharyngeal region of a patient;
   (b) selectively placing a second pair of electrodes in electrical contact with tissue of a pharyngeal region of a patient;
   (c) providing an apparatus for generating a series of electrical pulses for application of neuromuscular electrical stimulation to the patient through said first pair of electrodes, and for generating a series of electrical pulses for application of neuromuscular electrical stimulation to the patient through said second pair of electrodes, said apparatus comprising:
       (i) a first pulse generator for generating a first series of electrical pulses, each of which comprises a biphasic symmetrical waveform with an interval between the two phases, for output through a first channel;
       (ii) a first output jack for electrically connecting the first pair of electrodes to the first channel;
       (iii) a first intensity control circuit for regulating the first series of electrical pulses for output through the first channel such that the electrical current does not exceed a first predetermined value;
       (iv) a first frequency controller for controlling the frequency at which the series of electrical pulses is generated by the first pulse generator for output through the first channel so that such pulses are generated at a first predetermined frequency;
       (v) a first duration control circuit for controlling the duration of each electrical pulse generated by the first pulse generator;
       (vi) a second pulse generator for generating a second series of electrical pulses, each of which comprises a biphasic symmetrical waveform with an interval between the two phases, for output through a second channel;
       (vii) a second output jack for electrically connecting the second pair of electrodes to the second channel;
       (viii) a second intensity control circuit for regulating the second series of electrical pulses for output through the second channel such that the electrical current does not exceed a second predetermined value;
       (ix) a second frequency controller for controlling the frequency at which the series of electrical pulses is generated by the second pulse generator for output through the second channel so that such pulses are generated at a second predetermined frequency;
       (x) a second duration control circuit for controlling the duration of each electrical pulse generated by the second pulse generator;
   (d) connecting the first pair of electrodes to the first output jack;
   (e) connecting the second pair of electrodes to the second output jack;
   (f) generating a first series of electrical pulses, each of which comprises a biphasic symmetrical waveform with an interval between the two phases, for output through the first channel;
   (g) generating a second series of electrical pulses, each of which comprises a biphasic symmetrical waveform with an interval between the two phases, for output through the second channel;
   (h) providing the first series of electrical pulses through the first channel to the first pair of electrodes;
   (i) providing the second series of electrical pulses through the second channel to the second pair of electrodes.

10. An apparatus for generating a series of electrical pulses for application of neuromuscular electrical stimulation to a patient for treatment of oropharyngeal disorders, said apparatus comprising:
   (a) a first pair of electrodes;
   (b) a second pair of electrodes;
   (c) a first pulse generator for generating a first series of electrical pulses, each of which comprises a biphasic symmetrical waveform with an interval between the two phases, for output through a first channel;
   (d) a first intensity control circuit for regulating the first series of electrical pulses for output through the first channel such that the electrical current does not exceed a first predetermined value;
   (e) a first frequency controller for controlling the frequency at which the first series of electrical pulses is generated by the first pulse generator for output through the first channel so that such pulses are generated at a predetermined frequency;

(f) a first duration control circuit for controlling the duration of each electrical pulse generated by the first pulse generator;

(g) a second pulse generator for generating a second series of electrical pulses, each of which comprises a biphasic symmetrical waveform with an interval between the two phases, for output through a second channel;

(h) a second intensity control circuit for regulating the second series of electrical pulses for output through the second channel such that the electrical current does not exceed a second predetermined value;

(i) a second intensity control circuit for regulating the second series of electrical pulses for output through the second channel such that the electrical current does not exceed a second predetermined value;

(j) a second frequency controller for controlling the frequency at which the second series of electrical pulses is generated by the pulse generator for output through the second channel so that such pulses are generated at a predetermined frequency;

(k) a second duration control circuit for controlling the duration of each electrical pulse generated by the second pulse generator.

11. The apparatus of claim 10 wherein:

(a) the predetermined value for the electrical current of the first series of electrical pulses may be selectively set at a current level within the range of 0.5-25 mA; and (b) the predetermined value for the electrical current of the second series of electrical pulses may be selectively set at a current level within the range of 0.5-25 mA.

12. The apparatus of claim 10 wherein the frequency controller for each pulse generator controls the frequency at which the series of electrical pulses is generated for output through each channel so that such pulses are generated at a frequency of about 80 Hz.

13. The apparatus of claim 10 wherein the duration control circuit for each pulse generator controls the duration of each such electrical pulse so that each such pulse has a total pulse duration of about 550 to about 850 microseconds, which pulse duration includes an interphase interval of about 50 to about 150 microseconds.

14. The apparatus of claim 10 which includes:

(a) a first pair of electrodes, each of which comprises:
  (i) a snap eyelet having a first side and a second side, said second side having a connector to which a lead wire may be attached;
  (ii) a conductive film that is attached to the first side of the snap eyelet;
  (iii) an adhesive and conductive gel layer that is attached to the conductive film and adapted to be attached to the skin of the patient;

(b) a second pair of electrodes, each of which comprises:
  (i) a snap eyelet having a first side and a second side, said second side having a connector to which a lead wire may be attached;
  (ii) a conductive film that is attached to the first side of the snap eyelet;
  (iii) an adhesive and conductive gel layer that is attached to the conductive film and adapted to be attached to the skin of the patient;

(c) at least one adhesively backed tape overlay for securing at least one pair of electrodes to the skin of the patient.

* * * * *

UNITED STATES PATENT AND TRADEMARK OFFICE
CERTIFICATE OF CORRECTION

| | |
|---|---|
| PATENT NO. | : 7,280,873 B2 |
| APPLICATION NO. | : 10/782620 |
| DATED | : October 9, 2007 |
| INVENTOR(S) | : Marcy L. Freed et al. |

It is certified that error appears in the above-identified patent and that said Letters Patent is hereby corrected as shown below:

At column 17, lines 12-15, delete "(i) a second intensity control circuit for regulating the second series of electrical pulses for output through the second channel such that the electrical current does not exceed a second predetermined value";

At column 17, line 16, change "(j)" to --i--

At column 17, line 21, change "(k)" to --j--

Signed and Sealed this

Eleventh Day of December, 2007

JON W. DUDAS
*Director of the United States Patent and Trademark Office*